United States Patent [19]

Hlavka

[11] 4,112,219

[45] Sep. 5, 1978

[54] ACYL DERIVATIVES OF ANTIBIOTIC BM123γ

[75] Inventor: Joseph John Hlavka, Tuxedo Park, N.Y.

[73] Assignee: American Cyanamid Company, Stamford, Conn.

[21] Appl. No.: 815,340

[22] Filed: Jul. 13, 1977

[51] Int. Cl.² .......................................... C07H 13/12
[52] U.S. Cl. ................................. 536/17; 260/326.4; 260/326.44; 260/295 D; 424/180; 544/372
[58] Field of Search ........................................ 536/17

[56] References Cited

U.S. PATENT DOCUMENTS

| 4,018,972 | 4/1977 | Hlavka ..................................... 536/17 |
| 4,048,431 | 9/1977 | Hlavka et al. .......................... 536/17 |

*Primary Examiner*—Johnnie R. Brown
*Attorney, Agent, or Firm*—Edward A. Conroy, Jr.

[57] ABSTRACT

This disclosure describes a novel series of potent antibacterial agents derived by acylation of antibiotic BM123γ with N-acyloxysuccinimide derivatives.

10 Claims, No Drawings

ACYL DERIVATIVES OF ANTIBIOTIC BM123γ

BRIEF SUMMARY OF THE INVENTION

This invention relates to a novel group of antibiotics and, more particularly, is concerned with acylated derivatives of antibiotic BM123γ which may be represented by the following structural formula:

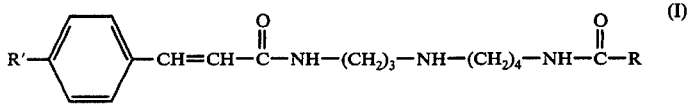

wherein R' is a moiety selected from the group consisting of those of the formulae:

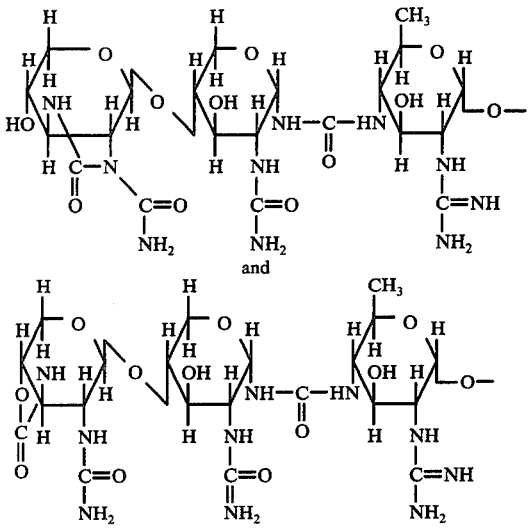

and R is hydrogen, lower alkyl, halo-substituted lower alkyl, straight chain alkyl having from 5 to 9 carbon atoms, cycloalkyl having from 3 to 6 carbon atoms, phenoxy-substituted lower alkyl, lower carboalkoxy, lower alkoxymethyl, styryl, pentachlorophenyl, pentafluorophenyl, 2,3,6-trichlorophenyl, 3,4,5-trimethoxyphenyl, 4-carbethoxy-3,5-dimethoxyphenyl, 1-naphthyl, 4-fluoro-1-naphthyl, 8-bromo-1-naphthyl, 2-naphthyl, 3-methoxy-2-naphthyl, 1-naphthyloxymethyl, 2-naphthyloxymethyl, trichloromethyl, chlorodiphenylmethyl, 2-pyridyl-N-oxide, 2-thienyl, 2-furyl, 1,4-thiapyran-2-yl, 4-oxy-4H-thiapyran-3-yl, 4-ethyl-2,3-diketopiperazin-1-yl or moieties of the formulae:

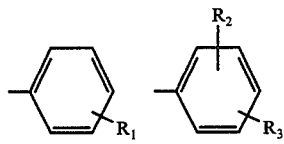

wherein $R_1$ is hydrogen, fluoro, chloro, bromo, nitro, cyano, hydroxy, mercapto, formyl, trifluoromethyl, trifluoromethoxy, phenyl, phenoxy, benzyl, benzoyl, sulfamyl, 4-chlorophenylsulfonyl, lower alkyl, lower alkoxy, lower alkylthio, lower alkanoyloxy, lower alkanoylamino or di(lower alkyl)-amino and $R_2$ and $R_3$ are the same and are fluoro, chloro, bromo, nitro, methyl or methoxy. Suitable lower alkyl, lower alkoxy, and lower alkythio groups contemplated by the present invention are those having up to four carbon atoms such as methyl, ethyl, tert-butyl, methoxy, iso-propoxy, n-butoxy, ethylthio, n-propylthio, sec-butylthio, etc. Suitable halo-substituted lower alkyl groups are those having up to four carbon atoms wherein halo is fluoro, chloro or bromo such as 2-bromoethyl, fluoromethyl, γ-chloropropyl, 4-fluorobutyl, etc. Suitable lower carboalkoxy and lower alkanoyl groups contemplated by the present invention are those having up to four carbon atoms such as carbomethoxy, carboisopropoxy, propionyl, isobutyryl, etc.

DETAILED DESCRIPTION OF THE INVENTION

The novel antibacterial agents of the present invention are organic bases and thus are capable of forming acid-addition salts with a variety of organic and inorganic salt-forming reagents. Thus, acid-addition salts, formed by admixture of the antibacterial free base with up to two equivalents of an acid, suitably in a neutral solvent, are formed with such acids as sulfuric, phosphoric, hydrochloric, hydrobromic, sulfamic, citric, maleic, fumaric, tartaric, acetic, benzoic, gluconic, ascorbic, and related acids. The acid-addition salts of the antibacterial agents of the present invention are, in general, crystalline solids relatively soluble in water, methanol and ethanol but are relatively insoluble in nonpolar organic solvents such as diethyl ether, benzene, toluene, and the like. For purposes of this invention, the antibacterial free bases are equivalent to their non-toxic acid addition salts.

The novel compounds of the present invention are derived by acylation of antibiotic BM123γ which has the formula:

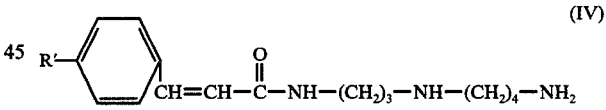

wherein R' is as hereinabove defined with an activated ester of the formula:

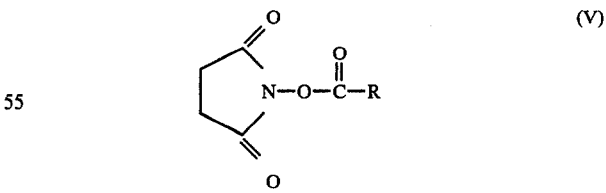

wherein R is as hereinabove defined. The acylation process may be preferably carried out as follows. Antibiotic BM123γ is dissolved in a suitable solvent such as methanol, dimethylformamide, ethanol, water, or dimethylsulfoxide; an amount of up to two equivalents of an activated ester is then added followed by the addition of a basic ion exchange resin such as Amberlite ® IR-45 or a trialkylated amine such as triethylamine or pyridine to maintain a slightly alkaline pH (7.5–8.7)

during the course of the reaction. After 30 minutes to 72 hours, with or without stirring at room temperature, the reaction mixture is filtered to remove the resin and the pH of the filtrate is adjusted to 6.8-7.0 with methanolic hydrochloric acid. The solvent volume is then reduced to 5-15 ml. in vacuo and the product is precipitated by the addition of from 35-100 ml. of acetone. The product is collected by filtration and dried in vacuo. After isolation, the product may be purified by any of the generally known methods for purification. These include recrystallization from various solvents and mixed solvent systems, chromatographic techniques, and counter current distribution, all of which are usually employed for this purpose.

The starting material for the acylation procedure has been defined hereinabove as antibiotic BM123γ having formula (IV). When R' is structure (II) in formula (IV), then the antibiotic is BM123γ$_1$ and when R' is structure (III) in formula (IV), then the antibiotic is BM123γ$_2$. The double bond of the cinnamamide moiety in formula (IV) may be cis or trans and hence there are four antibiotic starting materials, viz: cis-BM123γ$_1$, cis-BM123γ$_2$, trans-BM123γ$_1$, and trans-BM123γ$_2$. The preparation and properties of trans-BM123γ$_1$ and trans-BM123γ$_2$ are disclosed in U.S. Pat. No. 4,007,167 whereas the preparation and properties of cis-BM123γ$_1$ and cis-BM123γ$_2$ are set forth in U.S. Pat. No. 4,018,972. The term cis-BM123γ refers to a mixture in any proportion of cis-BM123γ$_1$ and cis-BM123γ$_2$ whereas the term trans-BM123γ refers to a mixture in any proportion of trans-BM123γ$_1$ and trans-BM123γ$_2$. The expression antibiotic BM123γ refers to either cis-BM123γ or trans-BM123γ. The usefulness of the acylated derivatives of antibiotic BM123γ is demonstrated by their ability to control systemic lethal infections in mice. These new substances show high in vivo antibacterial activity in mice against *Escherichia coli* US311 when administered by a single subcutaneous dose to groups of Carworth Farms CF-1 mice, weight about 20 grams, infected intraperitoneally with a lethal dose of this bacteria in a $10^{-3}$ trypticase soy broth TSP dilution of a 5 hour TSP blood culture. In Table I below is set forth the in vivo activity of typical products of this invention (prepared by the procedure of Example 1 from the indicated activated ester which was prepared by the procedure of Example 2 or Example 3) against *Escherichia coli* US311 in mice. The activity is expressed in terms of the ED$_{50}$ or the dose in mg./kg. of body weight required to protect 50% of the mice against *E. coli*. The derivative name in Table I indicates whether cis-BM123 or trans-BM123 was employed as starting material.

TABLE I

| Activated Ester Employed | Derivative Name | ED$_{50}$ in mg./kg. of Body Weight |
|---|---|---|
| N-(2-Fluorobenzoyloxy)succinimide | o-Fluorobenzoyl-trans-BM123γ | 1.0 |
| N-(p-Fluorobenzoyloxy)succinimide | p-Fluorobenzoyl-trans-BM123γ | 1.0 |
| N-(2-Thenoyloxy)succinimide | 2-Thienyl-trans-BM123γ | 1.0 |
| N-(2-Furoyloxy)succinimide | 2-Furyl-trans-BM123γ | 1.0 |
| N-(p-Anisoyloxy)succinimide | p-Methoxybenzoyl-trans-BM123γ | 1.0 |
| N-Trichloroacetyloxysuccinimide | Trichloroacetyl-trans-BM123γ | 1.0 |
| N-(2,4-Dichlorobenzoyloxy)succinimide | 2,4-Dichlorobenzoyl-trans-BM123γ | 0.5 1.0 |
| N-(p-Nitrobenzoyloxy)succinimide | p-Nitrobenzoyl-trans-BM123γ | 0.5 |
| N-(m-Fluorobenzoyloxy)succinimide | m-Fluorobenzoyl-trans-BM123γ | 1.0 |
| N-Pivaloyloxysuccinimide | Trimethylacetyl-trans-BM123γ | 1.0 |
| N-Carbethoxycarbonyloxysuccinimide | Carbethoxyformyl-trans-BM123γ | 1.0 |
| N-(m-Toluoyloxy)succinimide | m-Methylbenzoyl-trans-BM123γ | 1.0 |
| N-(3,4-Dichlorophenylcarbonyloxy)succinimide | 3,4-Dichlorobenzoyl-trans-BM123γ | 0.5 1.0 |
| N-(o-Toluoyloxy)succinimide | o-Methylbenzoyl-trans-BM123γ | 1.0 |
| N-(1-Naphthoyloxy)succinimide | 1-Naphthoyl-trans-BM123γ | 0.5 |
| N-Phenoxyacetoxysuccinimide | Phenoxyacetyl-trans-BM123γ | 1.0 |
| N-(2-Phenoxypropionyloxy)succinimide | α-Phenoxypropionyl-trans-BM123γ | 2.0 1.0 |
| N-(3,5-Dinitrophenylcarbonyloxy)succinimide | 3,5-Dinitrobenzoyl-trans-BM123γ | 1.0 |
| N-(o-Acetoxyphenylcarbonyloxy)succinimide | o-Acetoxybenzoyl-trans-BM123γ | 2.0 |
| N-(4-t-Butylphenylcarbonyloxy)succinimide | p-t-Butylbenzoyl-trans-BM123γ | 4.0 |
| N-(Ethylcarbonyloxy)succinimide | Propionyl-trans-BM123γ | 4.0 |
| N-(p-Cyanobenzoyloxy)succinimide | p-Cyanobenzoyl-trans-BM123γ | 4.0 |
| N-Chlorodiphenylacetoxysuccinimide | Chlorodiphenylacetyl-trans-BM123γ | 2.0 |
| N-(p-Trifluoromethylphenylcarbonyloxy)succinimide | p-Trifluoromethylbenzoyl-trans-BM123γ | 4.0 |
| N-Decanoyloxysuccinimide | Decanoyl-trans-BM123γ | 2.0 |
| N-(p-Chlorophenylcarbonyloxy)succinimide | p-Chlorobenzoyl-trans-BM123γ | 4.0 |
| N-(Benzoyloxy)succinimide | Benzoyl-trans-BM123γ | 4.0 |
| N-(Isopropylcarbonyloxy)succinimide | 2-Methylpropionyl-trans-BM123γ | 2.0 |
| N-Pentafluorophenylcarbonyloxysuccinimide | Pentafluorobenzoyl-trans-BM123γ | 0.5 |
| N-(2,6-Dimethoxyphenylcarbonyloxy)succinimide | 2,6-Dimethoxybenzoyl-trans-BM123γ | 2.0 |
| N-(Methoxymethylcarbonyloxy)succinimide | Methoxyacetyl-trans-BM123γ | 2.0 |
| N-(o-Hydroxyphenylcarbonyloxy)succinimide | o-Hydroxybenzoyl-trans-BM123γ | 8.0 |
| N-(α-Bromoethylcarbonyloxy)succinimide | α-Bromopropionyl-trans-BM123γ | 2.0 |
| N-(p-Methylthiophenylcarbonyloxy)succinimide | p-Methylthiobenzoyl-trans-BM123γ | 4.0 |
| N-(o-Mercaptophenylcarbonyloxy)succinimide | o-Mercaptobenzoyl-trans-MB123γ | 2.0 |
| N-[(2-Naphthoxy)methylcarbonyloxy]succinimide | 2-Napthyloxyacetyl-trans-BM123γ | 0.5 |
| N-(3,5-Dichlorophenylcarbonyloxy)succinimide | 3,5-Dichlorobenzoyl-trans-BM123γ | 0.5 |
| N-[1,4-thiapyran(2)carbonyloxy]succinimide | 1,4-Thiapyran(2)carbonyl-trans-BM123γ | 2.0 |
| N-(p-biphenylcarbonyloxy)succinimide | p-Biphenylcarbonyl-trans-BM123γ | 2.0 |
| N-(cinnamoyloxy)succinimide | Cinnamoyl-trans-BM123γ | 2.0 |
| N-(o-Benzylbenzoyloxy)succinimide | o-Benzylbenzoyl-trans-BM123γ | 2.0 |
| N-(m-Phenoxybenzoyloxy)succinimide | m-Phenoxybenzoyl-trans-BM123γ | 1.5 |
| N-(4-Carbethoxy-3,5-dimethoxybenzoyloxy)succinimide | 4-Carbethoxy-3,5-dimethoxybenzoyl-trans-BM123γ | 2.0 |
| N-Pentachlorobenzoyloxysuccinimide | Pentachlorobenzoyl-trans-BM123γ | 2.0 |
| N-(m-Hydroxybenzoyloxy)succinimide | m-Hydroxybenzoyl-trans-BM123γ | 1.5 |
| N-(p-Acetylbenzoyloxy)succinimide | p-Acetylbenzoyl-trans-BM123γ | 2.0 |
| N-(p-formylbenzoyloxy)succinimide | p-Formylbenzoyl-trans-BM123γ | 2.0 |
| N-(p-Hydroxybenzoyloxy)succinimide | p-Hydroxybenzoyl-trans-BM123γ | 2.0 |

TABLE I-continued

| Activated Ester Employed | Derivative Name | ED$_{50}$ in mg./kg. of Body Weight |
|---|---|---|
| N-(p-Acetaminobenzoyloxy)succinimide | p-Acetaminobenzoyl-trans-BM123γ | 2.0 |
| N-(Pyridine-n-oxide-2-carbonyloxy)succinimide | Pyridine-n-oxide-2-carbonyl-trans-BM123γ | 2.0 |
| N-(p-Dimethylaminobenzoyloxy)succinimide | p-Dimethylaminobenzoyl-trans-BM123γ | 2.0 |
| N-(o-Benzoylbenzoyloxy)succinimide | o-Benzoylbenzoyl-trans-BM123γ | 2.0 |
| N-(3,4-Dimethylbenzoyloxy)succinimide | 3,4-Dimethylbenzoyl-trans-BM123γ | 2.0 |
| N-(8-Bromo-1-napthoyloxy)succinimide | 8-Bromo-1-napthoyl-trans-BM123γ | 1.5 |
| N-(p-Ethoxybenzoyloxy)succinimide | p-Ethoxybenzoyl-trans-BM123γ | 2.0 |
| N-(p-Trifluoromethoxybenzoyloxy)succinimide | p-Trifluoromethoxybenzoyl-trans-BM123γ | 1.0 |
| N-(3-methoxy-2-naphthoyloxy)succinimide | 3-Methoxy-2-naphthoyl-trans-BM123γ | 2.0 |
| N-(o-Methylbenzoyloxy)succinimide | o-Methylbenzoyl-trans-BM123γ | 2.0 |
| N-(α-Phenoxypropionyloxy)succinimide | α-Phenyoxypropionyl-trans-BM123γ | 2.0 |
| N-(4-Oxy-4H-thiapran-3-yl-carbonyloxy)succinimide | 4-Oxy-4H-thiapran-3-yl-carbonyl-trans-BM123γ | 2.0 |
| N-Cyclopropylcarbonyloxysuccinimide | Cyclopropylcarbonyl-trans-BM123γ | 2.0 |
| N-m-Mercaptobenzoyloxy)succinimide | m-Mercaptobenzoyl-trans-BM123γ | 2.0 |
| N-(p-sulfamylbenzoyloxy)succinimide | p-Sulfamylbenzoyl-trans-BM123γ | 0.5 |
| N-(m-Bromobenzoyloxy)succinimide | m-Bromobenzoyl-trans-BM123γ | 0.75 |
| N-[4-(p-Chlorophenylsulfonyl)benzoyloxy]succinimide | 4-(p-Chlorophenylsulfonyl)-benzoyl-trans-BM123γ | 2.0 |
| N-(2,3,6-Trichlorobenzoyloxy)succinimide | 2,3,6-Trichlorobenzoyl-trans-BM123γ | 2.0 |
| N-(2,5-Dibromobenzoyloxy)succinimide | 2,5-Dibromobenzoyl-trans-BM123γ | 2.0 |
| N-(3,4,5-Trimethoxybenzoyloxy)succinimide | 3,4,5-Trimethoxybenzoyl-trans-BM123γ | 2.0 |
| N-(4-Fluoro-1-naphthoyloxy)succinimide | 4-Fluoro-1-naphthoyl-trans-BM123γ | 1.0 |
| N-(4-Ethyl-2,3-diketopyperazine-1-carbonyloxy)-succinimide | 4-Ethyl-2,3-diketopiperazine-1-carbonyl-trans-BM123γ | 2.0 |

A preferred embodiment of the present invention may be represented by formula (I) wherein the configuration of the double bond is trans, R' is as hereinabove defined, and R is hydrogen, alkyl having up to four carbon atoms, carboalkoxy having up to four carbon atoms or moieties of the formulae:

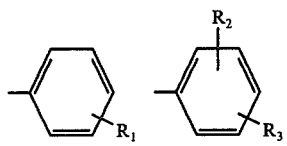

wherein R$_1$ is fluoro, chloro, nitro or alkyl having up to four carbon atoms and R$_2$ and R$_3$ are the same and are chloro or nitro.

The invention will be described in greater detail in conjunction with the following specific examples.

EXAMPLE 1

General Procedure for the Preparation of Acyl Derivatives of Antibiotic BM123γ

A 200 mg. portion of antibiotic cis-BM123γ or antibiotic trans-BM123γ is dissolved in 80 ml. of methanol and 300 mg. of the appropriate succinimide derivative is added. The pH is adjusted to about 8.0 with Amberlite ® IR-45 resin and the solution is stirred at room temperature for 1-2 hours. The resin is removed by filtration and the pH of the filtrate is adjusted to about 7.0 with methanolic HCl. The volume is then reduced to about 5 ml. in vacuo using a water aspirator. This solution is diluted with acetone. The resulting precipitate is recovered by filtration and dried in vacuo, resulting in the desired product.

EXAMPLE 2

General Procedure of the Preparation of Succinimide Derivatives

A 40 mmole portion of N-hydroxysuccinimide is dissolved in about 30 ml. of dry pyridine. A 40 mmole portion of the acid chloride of the desired acyl derivative (R-CO-Cl) is added in increments. The resulting suspension is stirred at room temperature for 24 hours and then evaporated to dryness. The residue is dissolved in 50 ml. chloroform and 25 ml. of water. The chloroform layer is washed with another 25 ml. of water, dried over MgSO$_4$, and the chloroform evaporated in vacuo giving an oily product which solidifies on standing.

EXAMPLE 3

General Procedure for the Preparation of Succinimide Derivatives Using N,N-Dicyclohexylcarbodiimide A 40 mmole portion of N-hydroxysuccinimide, 40 mmole of the desired organic acid (R-CO$_2$H), and 48 mmole of N,N-dicyclohexylcarbodiimide in 300 ml. of tetrahydrofuran is stirred at room temperature overnight. The so formed N,N-dicyclohexylurea is filtered and the filtrate is evaporated to dryness in vacuo yielding the desired activated ester.

EXAMPLE 4

Preparation of Trichloroacetyl-trans-BM123γ

A 4.6 gram portion of N-hydroxysuccinimide and 5.5 ml. of 2,2,2-trichloroethylchloroformate in 30 ml. of dry pyridine is reacted as described in Example 2. The product is recrystallized from diethyl ether giving 2,2,2-trichloroethyl carbonate succinimide. A 400 mg. portion of this product and 300 mg. of trans-BM123γ are reacted as described in Example 1 giving 273.9 mg. of trichloroacetyl-trans-BM123γ.

EXAMPLE 5

Preparation of Trimethylacetyl-trans-BM123γ

A 4.6 gram portion of N-hydroxysuccinimide and 5 ml. of trimethylacetyl chloride in 30 ml. of dry pyridine are reacted as described in Example 2 giving N-(pivaloyoxy)-succinimide. A 400 mg. portion of this product and 300 mg. of trans-BM123γ are reacted as described in Example 1, giving 227.7 mg. of trimethylacetyl-trans-BM123γ.

EXAMPLE 6

Preparation of Carboethoxyformyl-trans-BM123γ

A 2.04 gram portion of N-hydroxysuccinimide and 2.4 grams of ethyl oxalyl chloride in 25 ml. of dry pyridine are reacted as described in Example 2 giving N-(carbethoxycarbonyloxy)succinimide. A 300 mg. portion of this product and 200 mg. of trans-BM123γ are reacted as described in Example 1, giving 129.2 mg. of carboethoxyformyl-trans-BM123γ.

EXAMPLE 7

Preparation of Decanoyl-trans-BM123γ

A 4.6 gram portion of N-hydroxysuccinimide and 7.63 grams of decanoyl chloride in 30 ml. of dry pyridine are reacted as described in Example 2 giving N-(decanoyloxy)-succinimide. A 2 gram portion of this product and 1.5 grams of trans-BM123γ are reacted in 300 ml. of methanol as described in Example 1, giving 1.29 grams of decanoyl-trans-BM123γ.

EXAMPLE 8

Preparation of 1,4-Thiapyran(2)carbonyl-trans-BM123γ

A 0.7 gram portion of N-hydroxysuccinimide and 1.0 grams of 1,4-thiapyran(2)acid chloride in 35 ml of dry pyridine are reacted as described in Example 2 giving N-[1.4-thiapyran(2)carbonyloxy]succinimide. A 100 mg. portion of this product and 100 mg. of trans-BM123γ are reacted as described in Example 1, giving 70 mg. of 1,4-thiapyran(2)-carbonyl-trans-BM123γ.

EXAMPLE 9

Preparation of β-Phenylethylenecarbonyl-trans-BM123γ

A 3.03 gram portion of N-hydroxysuccinimide and 4.4 grams of cinnamoyl chloride in 40 ml. of dry pyridine are reacted as described in Example 2 giving N-(β-phenylethylenecarbonyloxy)succinimide. A 300 mg. portion of this product and 200 mg. of trans-BM123γ are reacted as described in Example 1, giving 150 mg. of β-phenylethylenecarbonyl-trans-BM123γ.

EXAMPLE 10

Preparation of p-Hydroxybenzoyl-cis-BM123γ

A 4.6 gram portion of N-hydroxysuccinimide and 7.0 grams of p-hydroxybenzoyl chloride in 4.4 ml. of dry pyridine and 30 ml. of dimethylformamide are reacted as described in Example 2 giving N-(p-hydroxylphenylcarbonyloxy)succinimide. A 400 mg. portion of this product and 300 mg. of cis-BM123γ are reacted as described in Example 1 giving the title product.

EXAMPLE 11

Preparation of p-Ethoxybenzoyl-cis-BM123γ

A 4.6 gram portion of N-hydroxysuccinimide and 6.90 grams of p-ethoxybenzoyl chloride in 30 ml. of dry pyridine are reacted as set forth in Example 2 giving N-(p-ethoxybenzoyl)succinimide. A 500 mg. portion of this product is reacted with 300 mg. of cis-BM123γ as described in Example 1 giving the title product.

EXAMPLE 12

Preparation of Pyridine-n-oxide-2-carbonyl-trans-BM123γ

A 4.6 g. portion of N-hydroxysuccinimide and 5.56 g. of picolinic acid N-oxide in 300 ml. of tetrahydrofuran were reacted as described in Example 3 giving N-(pyridine-N-oxide-2-carbonyloxy)succinimide. A 500 mg. portion of this product was reacted with 280 mg. of trans-BM123γ as described in Example 1 yielding the titled product.

EXAMPLE 13

8-Bromo-1-napthoyl-trans-BM123γ

A 540 mg. portion of N-hydroxysuccinimide and 1.2 g. of 8-bromo-1-napthoyl chloride in 35 ml. of pyridine were reacted as described in Example 2 giving N(8-Bromo-1-napthoyloxy)succinimide. A 400 mg. portion of this product was reacted with 300 mg. of trans-BM123γ as described in Example 1 yielding the titled product.

EXAMPLE 14

4-Oxy-4H-thiapyran-3-yl-carbonyl-trans-BM123γ

A 0.793 g. portion of N-hydroxysuccinimide and 1.0 g. of 4-oxy-4H-thiapyran-3-yl-carbonyl chloride in 35 ml of pyridine were reacted as described in Example 2 giving 150 mg. of N-(4-oxy-4H-thiapyran-3-yl-carbonyloxy)succinimide. A 100 mg. portion of this product was reacted with 100 mg. of trans-BM123γ as described in Example 1 yielding the titled product.

EXAMPLE 15

Cyclopropyl carbonyl-trans-BM123γ

A 4.6 g. portion of N-hydroxysuccinimide and 4.18 g. of cyclopropanecarboxylic acid chloride in 50 ml. of pyridine were reacted as described in Example 2 giving 6.6 g. of N-Cyclopropylcarbonyloxysuccinimide. A 400 mg. portion of this product was reacted with 300 mg. of trans-BM123γ as described in Example 1 yielding the titled product.

EXAMPLE 16 m-Mercaptobenzoyl-trans-BM123γ

A 4.6 g. portion of N-hydroxysuccinimide and 8.0 g. of m-thiobenzoyl chloride in 4.4 ml. of pyridine and 30 ml. of DMF were reacted as described in Example 2 giving 12 g. of N-(m-mercaptobenzoyloxy)succinimide. A 400 mg. portion of this product was reacted with 300 mg. of trans-BM123γ as as described in Example 1 yielding the titled product.

EXAMPLE 17

4-Ethyl-2,3-diketopiperazine-1-carbonyl-trans-BM123γ

A 3.0 g. portion of N-hydroxysuccinimide and 5.5 g. of 4-ethyl-2,3-diketopiperazine-1-carbonyl chloride in 20 ml. of pyridine were reacted as described in Example 2 giving N-(4-Ethyl-2,3-diketopiperazine-1-carbonyloxy)succinimide. A 400 mg. portion of this product was reacted with 200 mg. of trans-BM123γ as described in Example 1 yielding the titled product.

I claim:

1. A compound selected from the group consisting of those of the formula:

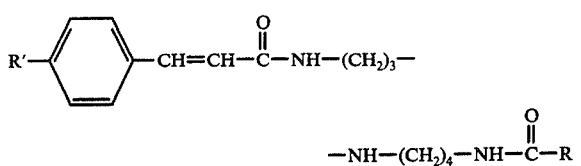

wherein the configuration of the double bond is cis or trans; R' is a moiety selected from the group consisting of those of the formulae:

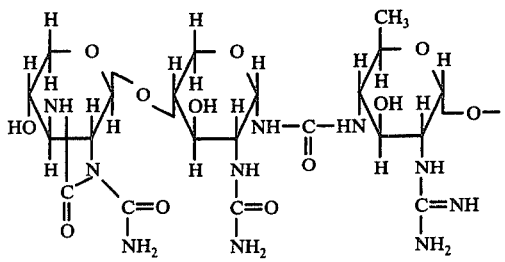

and

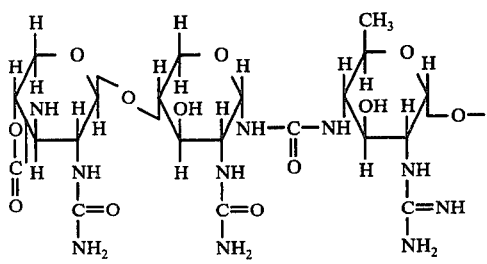

and R is selected from the group consisting of hydrogen, lower alkyl, halo-substituted lower alkyl, straight chain alkyl having from 5 to 9 carbon atoms, cycloalkyl having from 3 to 6 carbon atoms, phenoxy-substituted lower alkyl, lower carboalkoxy, lower alkoxymethyl, styryl, pentachlorophenyl, pentafluorophenyl, 2,3,6-trichlorophenyl, 3,4,5-trimethoxyphenyl, 4-carbethoxy-3,5-dimethoxyphenyl, 1-naphthyl, 4-fluoro-1-naphthyl, 8-bromo-1-naphthyl, 2-naphthyl, 3-methoxy-2-naphthyl, 1-naphthyloxymethyl, 2-naphthyloxymethyl, trichloromethyl, chlorodiphenylmethyl, 2-pyridinyl-N-oxide, 2-thienyl, 2-furyl, 1,4-thiapyran-2-yl, 4-oxy-4H-thiapyran-3-yl, 4-ethyl-2,3-diketopiperazin-1-yl or moieties of the formulae:

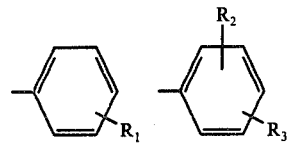

wherein $R_1$ is hydrogen, fluoro, chloro, nitro, cyano, hydroxy, mercapto, formyl, trifluoromethyl, trifluoromethoxy, phenyl, phenoxy, benzyl, benzoyl, sulfamyl, 4-chlorophenylsulfonyl, lower alkyl, lower alkoxy, lower alkylthio, lower alkanoyloxy, lower alkanoylamino or di(lower akyl)-amino and $R_2$ and $R_3$ are the same and are fluoro, chloro, nitro, methyl or methoxy; and the pharmacologically acceptable acid-addition salts thereof.

2. A mixture consisting essentially of a compound according to claim 1 wherein the double bond is cis and R' is moiety (A) and a compound according to claim 1 wherein the double bond is cis and R' is moiety (B) and R is the same in both compounds.

3. A mixture consisting essentially of a compound according to claim 1 wherein the double bond is trans and R' is moiety (A) and a compound according to claim 1 wherein the double bond is trans and R' is moiety (B) and R is the same in both compounds.

4. The mixture in accordance with claim 2 wherein R is 2,4-dichlorophenyl; 2,4-dichlorobenzoyl-cis-BM123γ.

5. The mixture in accordance with claim 2 wherein R is p-nitrophenyl; p-nitrobenzoyl-cis-BM123γ.

6. The mixture in accordance with claim 3 wherein R is 3,4-dichlorophenyl; 3,4-dichlorobenzoyl-trans-BM123γ.

7. The mixture in accordance with claim 3 wherein R is 1-naphthyl; 1-naphthoyl-trans-BM123γ.

8. The compound in accordance with claim 1 wherein the double bond is cis, R' is moiety (A), and R is pentafluorophenyl; pentafluorobenzoyl-cis-BM123γ$_1$.

9. The compound in accordance with claim 1 wherein the double bond is trans, R' is moiety (B), and R is 2-naphthyloxymethyl; 2-naphthyloxyacetyl-trans-BM123γ$_2$.

10. The compound in accordance with claim 1 wherein the double bond is trans, R' is moiety (B), and R is 3,5-dichlorophenyl; 3,5-dichlorobenzoyl-trans-BM123γ$_2$.

* * * * *